(12) United States Patent
Morey et al.

(10) Patent No.: US 11,771,451 B2
(45) Date of Patent: *Oct. 3, 2023

(54) MEDICAL DEVICES AND RELATED METHODS

(71) Applicant: Boston Scientific Limited, Galway (IE)

(72) Inventors: Subodh Morey, Goa (IN); Ashish Jain, Uttar Pradesh (IN); Sumit Malik, Haryana (IN); Rajivkumar Singh, Maharashtra (IN); Aditya Dhanotiya, Madhya Pradesh (IN); Mark Voss, Spencer, IN (US)

(73) Assignee: Boston Scientific Limited, Galway (IE)

( * ) Notice: Subject to any disclaimer, the term of this patent is extended or adjusted under 35 U.S.C. 154(b) by 106 days.

This patent is subject to a terminal disclaimer.

(21) Appl. No.: 17/374,105

(22) Filed: Jul. 13, 2021

(65) Prior Publication Data

US 2021/0338257 A1 Nov. 4, 2021

Related U.S. Application Data

(63) Continuation of application No. 16/298,223, filed on Mar. 11, 2019, now Pat. No. 11,090,072.

(Continued)

(51) Int. Cl.
*A61B 17/221* (2006.01)
*A61B 17/00* (2006.01)
(Continued)

(52) U.S. Cl.
CPC ........ *A61B 17/221* (2013.01); *A61B 17/2909* (2013.01); *A61B 2017/00367* (2013.01);
(Continued)

(58) Field of Classification Search
CPC ... A61B 17/221; A61B 17/29; A61B 17/2909; A61B 2017/00367; A61B 2017/00424;
(Continued)

(56) References Cited

U.S. PATENT DOCUMENTS

4,872,456 A 10/1989 Hasson
4,898,574 A * 2/1990 Uchiyama ........ A61B 17/32037
606/127

(Continued)

FOREIGN PATENT DOCUMENTS

| CN | 204581411 | 8/2015 |
| DE | 24 28 319 | 1/1976 |
| WO | WO 96/04875 | 2/1996 |

OTHER PUBLICATIONS

International Search Report and Written Opinion issued in International Application No. PCT/IB2019/051964, dated Jun. 3, 2019 (13 pages).

*Primary Examiner* — Kankindi Rwego
(74) *Attorney, Agent, or Firm* — Bookoff McAndrews, PLLC

(57) ABSTRACT

A medical device includes a handle with a proximal arm and a distal arm. The proximal arm and the distal arm are pivotable via a joint. The medical device also includes a tube coupled to the distal arm and a drive wire. A distal portion of the drive wire includes an expandable end effector. A portion of the drive wire is positioned within the tube, and a different portion of the drive wire extends proximally of the distal arm and is coupled to the proximal arm.

14 Claims, 7 Drawing Sheets

Related U.S. Application Data

(60) Provisional application No. 62/641,808, filed on Mar. 12, 2018, provisional application No. 62/641,822, filed on Mar. 12, 2018.

(51) Int. Cl.
*A61M 25/00* (2006.01)
*A61B 17/29* (2006.01)

(52) U.S. Cl.
CPC ............ *A61B 2017/00424* (2013.01); *A61B 2017/2212* (2013.01); *A61B 2017/2217* (2013.01); *A61B 2017/292* (2013.01); *A61B 2017/2918* (2013.01); *A61B 2017/2929* (2013.01); *A61M 25/0074* (2013.01)

(58) Field of Classification Search
CPC .... A61B 2017/2212; A61B 2017/2215; A61B 2017/2217; A61B 2017/2918; A61B 2017/292; A61B 2017/2929

USPC ........................................................ 606/127
See application file for complete search history.

(56) References Cited

U.S. PATENT DOCUMENTS

| | | |
|---|---|---|
| 4,909,789 A | 3/1990 | Taguchi et al. |
| 5,197,968 A | 3/1993 | Clement |
| 6,235,026 B1 | 5/2001 | Smith |
| 6,375,635 B1 * | 4/2002 | Moutafis ............ A61B 17/3203 604/35 |
| 6,997,867 B2 | 2/2006 | Soble et al. |
| 8,043,303 B2 | 10/2011 | Razvi et al. |
| 2005/0261705 A1 | 11/2005 | Gist |
| 2006/0247495 A1 | 11/2006 | Bacher et al. |
| 2009/0030427 A1 | 1/2009 | Razvi et al. |
| 2014/0309655 A1 | 10/2014 | Gal et al. |
| 2016/0022289 A1 | 1/2016 | Wan |
| 2017/0209162 A1 | 7/2017 | Sperry et al. |

\* cited by examiner

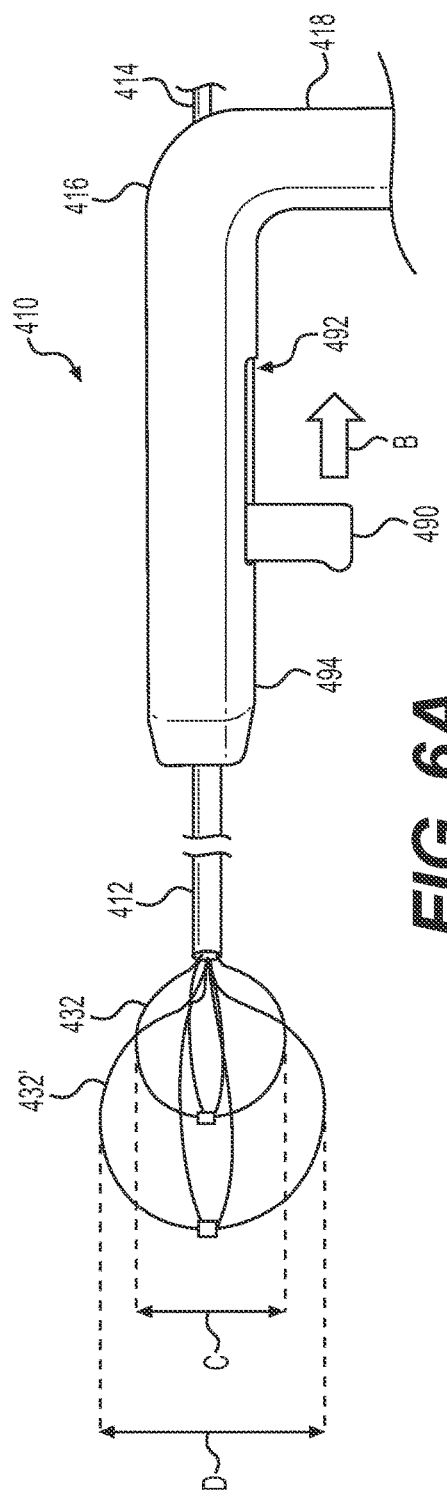
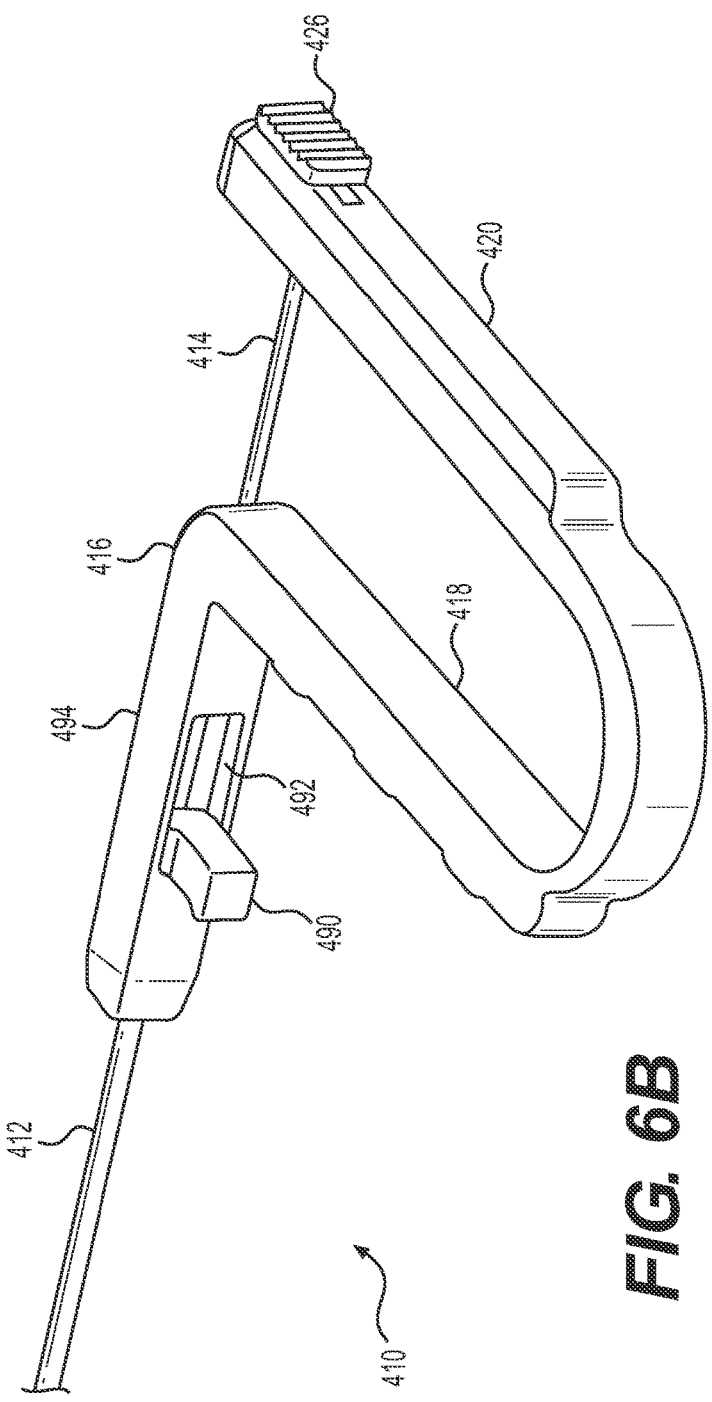
FIG. 6A
FIG. 6B

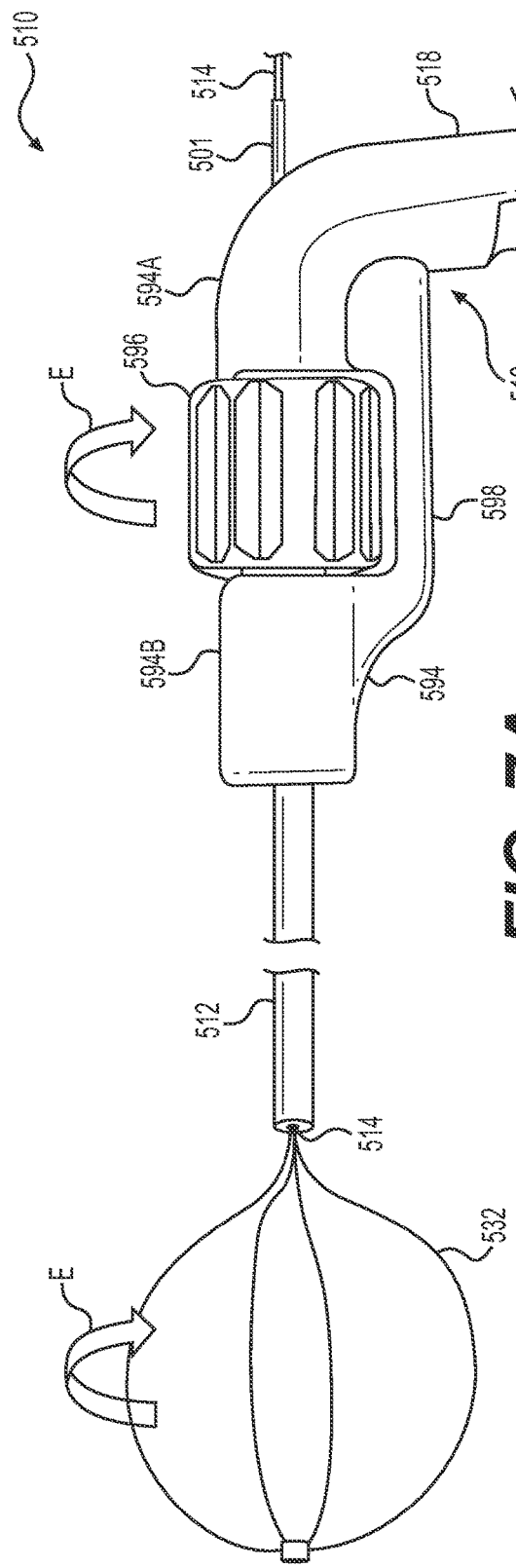
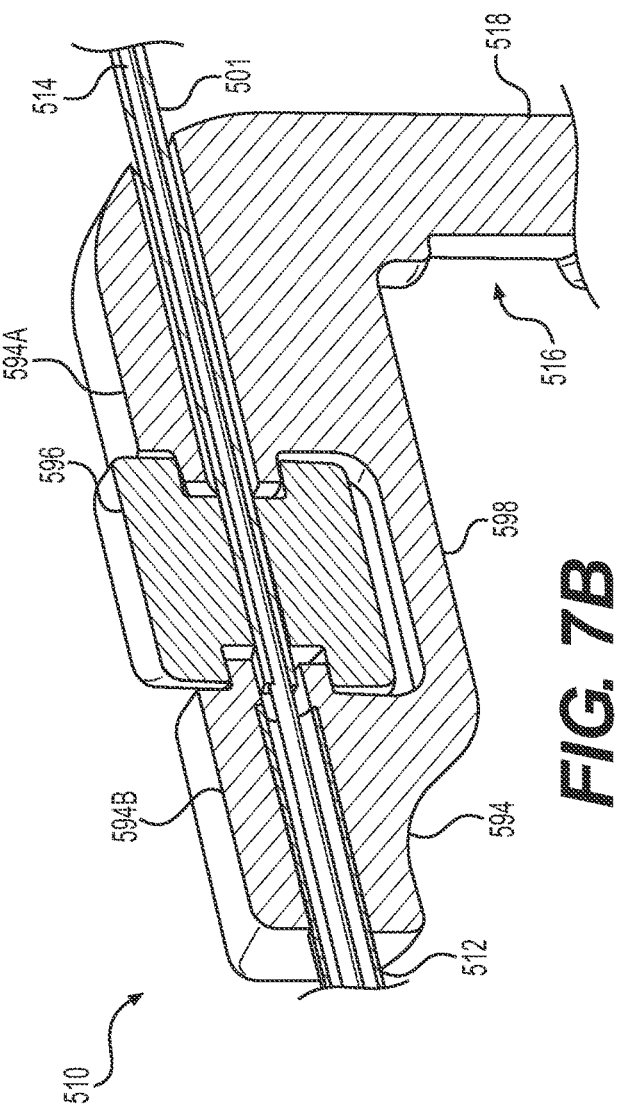

MEDICAL DEVICES AND RELATED METHODS

CROSS-REFERENCE TO RELATED APPLICATIONS

This patent application is continuation of U.S. application Ser. No. 16/298,223, filed Mar. 11, 2019, which claims the benefit of priority under 35 U.S.C. § 119 to U.S. Provisional Patent Application No. 62/641,808 and U.S. Provisional Patent Application No. 62/641,822, both filed on Mar. 12, 2018, all of which are herein incorporated by reference in their entireties.

TECHNICAL FIELD

Various aspects of the present disclosure relate generally to medical devices and related methods. More specifically, the present disclosure relates to medical devices and methods for providing and regulating irrigation and/or suction in a medical retrieval procedure.

BACKGROUND

Medical procedures to remove material, such as a kidney stone, from a patient often use an expandable basket device. For example, during a percutaneous nephrolithotomy ("PCNL") procedure, a user may apply energy, for example, with a pneumatic or ultrasonic probe through a nephroscope or other insertion device, to a kidney stone to break-up or reduce the size of the kidney stone. Then, the user may remove smaller fragments with suction applied through a suction tube, and the user may remove larger fragments with a basket device. The user may repeatedly apply the suction and actuate the basket device based on the size and/or number of kidney stone particles and other material to be removed. The procedure may require additional energy application and/or irrigation as well. However, using different medical devices requires the user to continuously exchange the long medical devices through the insertion device. Exchanging and positioning the different medical devices may increase the duration and risks of the procedure.

Additionally, if the stone or material is captured in a basket device but is too large to be removed, it may be necessary to apply energy to the stone within the basket device. The basket sheath may occupy much of the cross-sectional area within the insertion device, preventing insertion of the energy device to target the stone. Therefore, the user may seek to remove the basket sheath from the insertion device without removing the basket drive wire. However, the user may be holding the insertion device and the basket device, so removing the basket sheath would require an additional medical professional, further increasing the duration and risks of the procedure.

The devices and methods of the current disclosure may rectify some of the deficiencies described above, and/or address other aspects of the prior art.

SUMMARY

Examples of the present disclosure relate to, among other things, medical devices and methods. Each of the examples disclosed herein may include one or more of the features described in connection with any of the other disclosed examples.

In one example, a medical device may include a handle with a proximal arm and a distal arm. The proximal arm and the distal arm may be pivotable via a joint. The medical device also may include a tube coupled to the distal arm and a drive wire. A distal portion of the drive wire may include an expandable end effector. A portion of the drive wire may be positioned within the tube, and a different portion of the drive wire may extend proximally of the distal arm and may be coupled to the proximal arm.

The medical device may further include one or more of the following features. A proximal end of the drive wire may be releasably coupled to the proximal arm via a drive wire clip. The drive wire clip may be depressible and slotted, and the drive wire clip may be movable in a direction transverse to the drive wire to uncouple the drive wire from the proximal arm. The drive wire clip may be biased toward an extended position by a spring within the proximal arm. The medical device may be configured to be held in a user's hand, and the drive wire clip may be configured to be actuated by a thumb of the user's hand.

The medical device may further include a lever, and the tube may be fixedly coupled to the lever. The lever may be slidably positioned within a slot in an extension extending distally from the distal arm. When the proximal arm and the distal arm are compressed together, the expandable end effector may extend from a distal end of the tube to form a first size or shape, and proximal movement of the lever when the proximal arm and the distal arm are compressed may further expand the expandable end effector to form a second size or shape. The medical device may be configured to be held in a user's hand, and the lever may be configured to be actuated by a finger of the user's hand.

The medical device may further include a distal extension extending distally from the distal arm. The distal extension may include a proximal portion and a distal portion, and the proximal portion and the distal portion may be connected by at least one bridge element. The medical device may further include a rotary knob positioned between the proximal portion and the distal portion of the distal extension, and the rotary knob may radially surround a portion of the drive wire. The medical device may further include a shaft element positioned radially between the drive wire and the rotary knob, and the shaft element may be fixedly coupled to the drive wire. The shaft element and the rotary knob may each include at least one engaging surface such that rotation of the rotary knob in a first direction causes the shaft element to also rotate in the first direction. The shaft element may slide freely in a longitudinal direction through the rotary knob, and rotation of the rotary knob in the first direction may cause the drive wire and the expandable end effector to also rotate in the first direction.

In another example, a medical device may include a handle including a proximal arm, a distal arm, a distal extension extending from the distal arm, and a lever slidably positioned within a slot in a portion of the distal extension. The medical device may also include a tube positioned within a portion of the distal extension and fixedly coupled to the lever, and proximal movement of the lever may move the tube proximally. The medical device may further include a drive wire, and a distal portion of the drive wire may include an expandable retrieval device. A portion of the drive wire may be positioned within the tube, and a different portion of the drive wire may extend proximally of the distal arm and may be coupled to the proximal arm.

The medical device may further include one or more of the following features. A proximal end of the drive wire may be releasably coupled to the proximal arm via a drive wire clip. The drive wire clip may be depressible and slotted, and the drive wire clip may be movable in a direction transverse to the drive wire to uncouple the drive wire from the proximal arm. The drive wire clip may be biased toward an extended position by a spring within the proximal arm. The medical device may be configured to be held in a user's hand, and the drive wire clip may be configured to be actuated by a thumb of the user's hand.

In a further example, a medical device may include a handle including a proximal arm, a distal arm, a distal extension extending from the distal arm, and a rotary knob partially surrounded by one or more portions of the distal extension. The medical device may also include a tube coupled to the distal extension distal to the rotary knob, and a drive wire coupled to an end effector. A portion of the drive wire may be positioned within the tube, and a different portion of the drive wire may extend proximally of the distal arm and may be coupled to the proximal arm. The medical device may further include a shaft element radially surrounding and fixedly coupled to a portion of the drive wire, and the shaft element may be positioned radially between a portion of the drive wire and the rotary knob.

The medical device may further include one or more of the following features. The shaft element and the rotary knob may each include at least one engaging surface such that rotation of the rotary knob in a first direction causes the shaft element to also rotate in the first direction. The end effector may include an expandable retrieval basket, and the shaft element may slide freely in a longitudinal direction through the rotary knob. Rotation of the rotary knob in the first direction may cause the drive wire and the expandable retrieval basket to rotate in the first direction.

Both the foregoing general description and the following detailed description are exemplary and explanatory only and are not restrictive of the features, as claimed. As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value.

BRIEF DESCRIPTION OF THE FIGURES

The accompanying drawings, which are incorporated in and constitute a part of this specification, illustrate various exemplary embodiments and together with the description, serve to explain the principles of the disclosure.

FIG. 6A illustrates a side view of a portion of an additional medical device, and FIG. 6B illustrates a perspective view of a portion of the additional medical device, according to additional aspects of the present disclosure.

FIG. 7A illustrates a side view of a portion of yet another medical device, and FIG. 7B illustrates a cross-sectional view of a portion of the medical device, according to further aspects of the present disclosure.

DETAILED DESCRIPTION

Examples of the present disclosure include devices and methods to facilitate, and improve the efficacy and safety of minimally-invasive surgeries. For example, aspects of the present disclosure may relate to medical devices and methods for delivering irrigation or suction during a medical procedure with an additional medical device, such as, for example, a procedure to remove kidney stones or other material from a patient's kidney or other organ via PCNL with a retrieval basket device. In some embodiments, for example, the medical devices of the present disclosure may include or be used with any appropriate insertion sheath, nephroscope, and/or any appropriate medical device to deliver treatment.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively farther away from the operator using the medical device or insertion device, or closer to the interior of the body.

Figure 1:
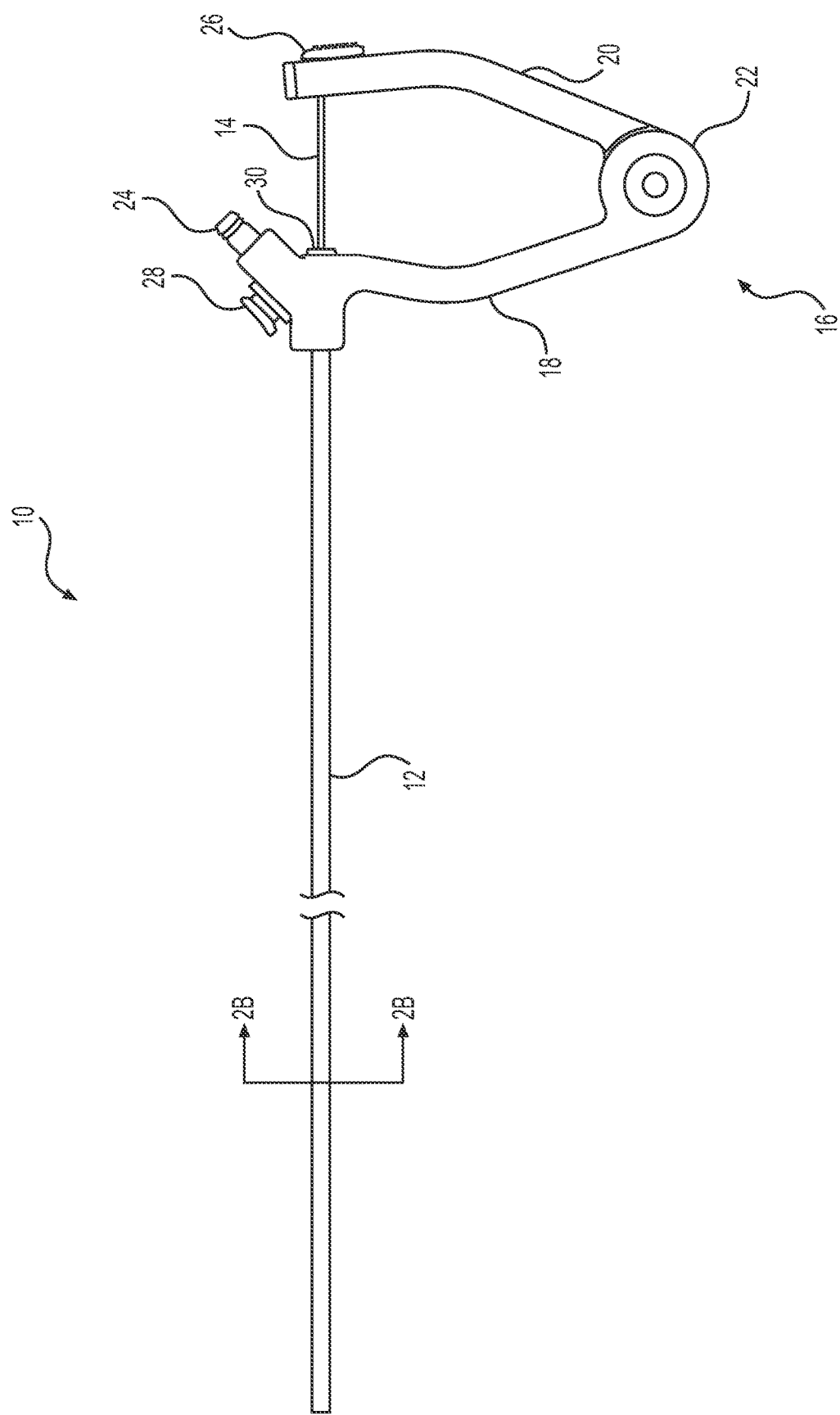
FIG. 1 illustrates a medical device, according to aspects of the present disclosure.

FIG. 1 illustrates a medical device 10 that includes outer tube 12, a drive wire 14, and a handle 16. Although not shown, medical device 10 includes an inner tube (FIGS. 2A and 2B) positioned within outer tube 12 and at least partially enclosing drive wire 14. Handle 16 includes a distal arm 18 and a proximal arm 20, with distal arm 18 and proximal arm 20 being at least partially pivotable relative to each other via joint 22. Outer tube 12 is secured within distal arm 18, and distal arm 18 also includes a port 24 such that irrigation or suction may be delivered via port 24 through outer tube 12. Drive wire 14 is coupled to proximal arm 20 such that pivoting or compression of proximal arm 20 towards or relative to distal arm 18 causes drive wire 14 to extend distally through the inner tube and outer tube 12.

Outer tube 12 may be a rigid sheath or hollow shaft. An inner tube 34 (FIGS. 2A and 2B) at least partially encloses drive wire 14 and is positioned within outer tube 12. In one aspect, inner tube 34 may be secured to an inner portion of outer tube 12, for example, by an adhesive, laser welding, or other connections.

Figures 2A, 2B:
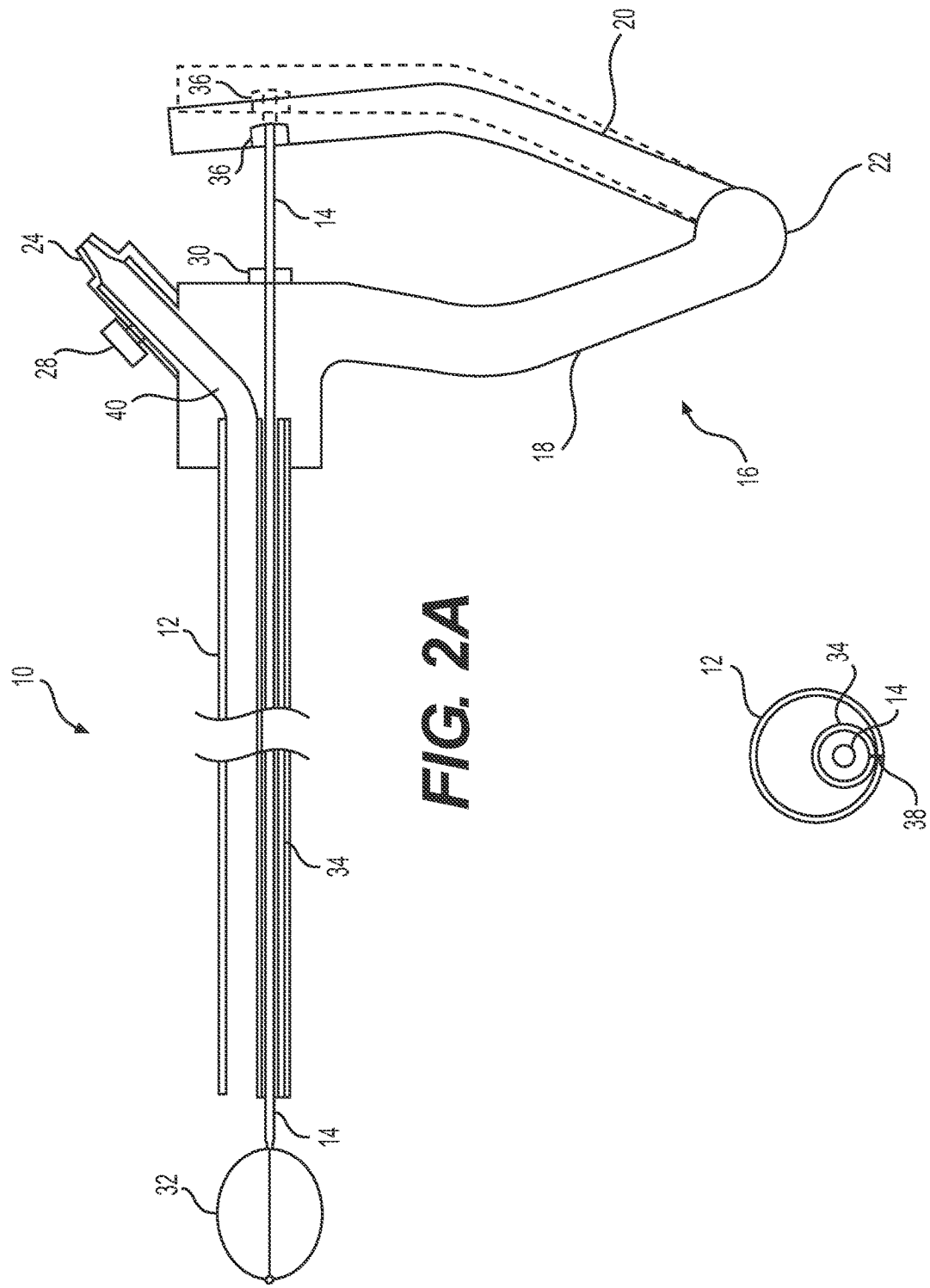
FIG. 2A illustrates a schematic view of an axial cross-section of the medical device of FIG. 1.
FIG. 2B illustrates an cross-sectional view of a portion of the medical device of FIG. 1, according to aspects of the present disclosure.

Drive wire 14 may include an expandable end effector. For example, as shown in FIG. 2A, a self-expandable retrieval basket 32 may be coupled to the distal end of drive wire 14. Therefore, as proximal arm 20 of handle 16 pivots relative to distal arm 18, self-expandable retrieval basket 32 may extend distally of the inner tube and outer tube 12 and expand, for example, to capture a kidney stone or other material to be removed. Drive wire 14 may be coupled to proximal arm 20 of handle 16 via a drive wire clip 26. In one aspect, drive wire clip 26 may be operable to disconnect drive wire 14 from handle 16 in order to further extend, further retract, or otherwise uncouple drive wire 14, as may be necessary in various medical procedures.

As mentioned, handle 16 includes distal arm 18 and proximal arm 20 coupled at joint 22. In one aspect, joint 22 may be a portion of distal arm 18 (as shown), may be a portion of proximal arm 20, or may be a separate element. Joint 22 may include a torsion spring or other biasing member (not shown) such that handle 16 may be biased to return to an equilibrium position. For example, a user may hold handle 16 with one hand, and may squeeze handle 16 to compress and move proximal arm 20 toward distal arm 18 in order to extend drive wire 14 distally relative to outer tube 12.

Handle 16 includes port 24. Port 24 is connected to outer tube 12, for example, through a portion of distal arm 18, for example, through an internal lumen 40 as shown in FIG. 2A. A suction or irrigation source may be coupled to port 24 to deliver the suction or irrigation through outer tube 12. Port 24 may include threads, gaskets, etc. to ensure a secure, air-tight connection between handle 16 and a tube connecting the suction or irrigation source.

Handle 16 may also include a mechanism, such as a button or trigger 28, on distal arm 18 to open or close an internal connection between port 24 and outer tube 12. For example, trigger 28 may be spring-biased and operable to open or close the connection between port 24 and outer tube 12. In an extended position, trigger 28 may close the connection between port 24 and outer tube 12 such that no suction or irrigation is introduced into outer tube 12. In a depressed position, trigger 28 may open the connection between port 24 and outer tube 12 such that the suction or irrigation is introduced into outer tube 12.

In an alternative example, trigger 28 may include a variable opening such that the degree to which trigger 28 is depressed and/or the amount of pressure applied to trigger 28 is correlated to the size of the opening between port 24 and outer tube 12. The size of the opening may then correspond to the amount or pressure of the suction or irrigation delivered through outer tube 12. In an additional aspect, trigger 28 may be operably replaced by a rotatable dial. In a further aspect, trigger 28 may be operably replaced by a foot pedal wirelessly or wired connected to handle 16 to control the opening between port 24 and outer tube 12.

Furthermore, trigger 28 may include a locking mechanism (not shown) such that a user may selectively lock trigger 28 in a depressed configuration such that the irrigation or suction may be delivered through outer tube 12 without the user maintaining his or her finger on trigger 28. It is also noted that with trigger 28 depressed, port 24 and outer tube 12 may provide a working channel. For example, with trigger 28 depressed and without a suction or irrigation source coupled to port 24, a laser fiber, forceps, or other medical element may be inserted through port 24 and delivered to the patient lumen through outer tube 12. In another aspect, port 24 may include a Y-connector. In this aspect, a suction or irrigation source may be coupled to one port of the Y-connector, and a laser fiber, forceps, or other medical element may be inserted through the other port of the Y-connector and delivered to the patient lumen. Alternatively, handle 16 may not include trigger 28, and port 24 and outer tube 12 may provide a working channel for an additional medical device. In any of the above aspects, port 24 may also include a seal or other elements to help prevent a backflow of irrigation or bodily fluids.

Handle 16 may further include a seal 30 positioned at a proximal end of distal arm 18. Seal 30 may surround a portion of drive wire 14. As such, drive wire 14 may move within handle 16 with a reduced risk of irrigation or bodily fluids escaping from medical device 10 or the user contaminating the patient's lumen during the procedure.

FIG. 2A illustrates a schematic cross-sectional view of medical device 10 with handle 16 in a compressed position and drive wire 14 extended distally beyond outer tube 12 to extend an expandable retrieval basket 32. The uncompressed position of handle 16 is shown in dashed lines. FIG. 2A illustrates an inner tube 34 positioned within outer tube 12 and enclosing a portion of drive wire 14. Inner tube 34 is shown as extending the length of outer tube 12, but inner tube 34 may also extend proximally of outer tube 12, for example, to seal 30. It is noted that FIG. 2A does not show drive wire clip 26, but illustrated drive wire 14 being coupled to proximal arm 20 via a slot 36.

FIG. 2B illustrates an cross-sectional view of medical device 10. As such, FIG. 2B shows inner tube 34 coupled within outer tube 12 via coupling 38. Drive wire 14 is positioned within inner tube 34. As mentioned above, in one aspect, coupling 38 may be formed by laser-welding outer tube 12 and inner tube 34 together.

In one aspect, a user may hold distal arm 18 and proximal arm 20 of handle 16 in the user's left or right hand. The user may contract his or her hand, which pivots proximal arm 20 relative to distal arm 18, as shown in FIG. 2A. Pivoting distal arm 20 toward proximal arm 18 extends drive wire 14 distally through seal 30 and beyond distal ends of outer tube 12 and inner tube 34, expanding retrieval basket 32.

Distal arm 18 of handle 16 also includes an internal lumen 40 connecting port 24 to outer tube 12. Internal lumen 40 may be angled (FIG. 2A). Although not shown, internal lumen 40 may include an adjustable seal or connection that may be controlled by trigger 28 to open or close internal lumen 40. For example, internal lumen 40 may include a pinching tube that closes internal lumen 40, and actuating trigger 28 may open the pinching tube and open internal lumen 40. Alternatively, internal lumen 40 may be flexible, and actuating trigger 28 may compress the walls of internal lumen 40 to close internal lumen 40. Moreover, internal lumen 40 provides a conduit for a user to deliver irrigation, suction, or another medical device through port 24 and outer tube 12 to treat a patient.

Figure 3:
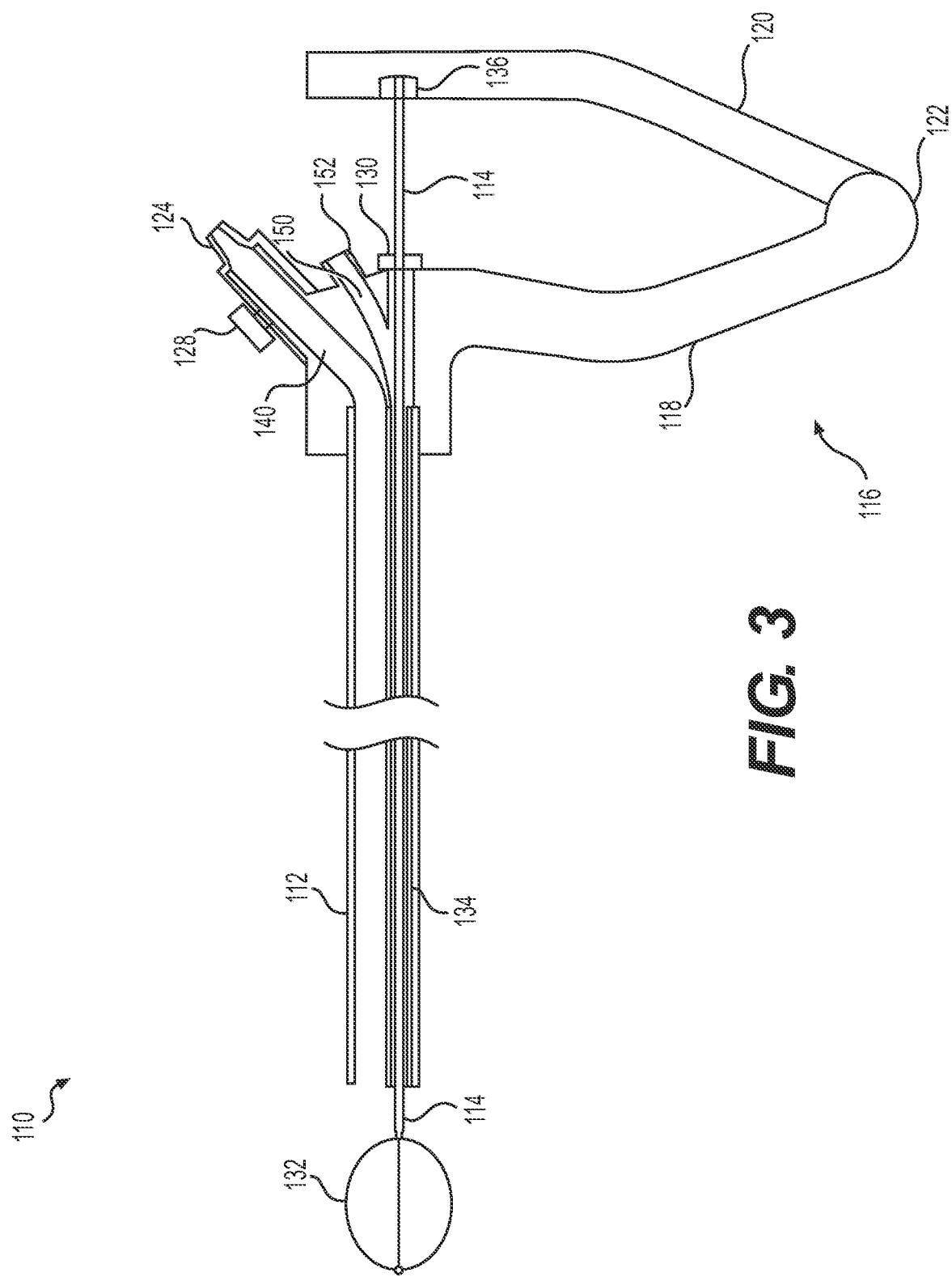
FIG. 3 illustrates a schematic view of an axial cross-section of a further exemplary medical device, according to aspects of the present disclosure.

FIG. 3 illustrates an alternative example according to present disclosure, with similar elements to medical device 10 shown by 100 added to the reference numbers. Medical device 110 includes outer tube 112, inner tube 134, and drive wire 114 coupled to handle 116, and movement of distal arm 118 and proximal arm 120 relative to each other extends drive wire 114 distally beyond outer tube 112 and inner tube 134. Similarly, handle 116 includes port 124 such that irrigation, suction, or an additional medical device may be delivered through internal lumen 140 and outer tube 112 to treat a patient.

In addition to internal lumen 140, medical device 110 includes an inner tube lumen 150 within distal arm 118. Inner tube lumen 150 may connect inner tube 134 to an inner tube port 152. In one aspect, inner tube lumen 150 may include two branches, with a first branch connecting to inner tube port 152, and a second branch connecting to seal 130. A suction or irrigation source (not shown) may be coupled to inner tube port 152, in the same manner as discussed above with respect to port 24. The suction or irrigation may be activated to surround drive wire 114 within inner tube 134. Furthermore, as with port 24, although not shown, handle 116 may further include an additional mechanism operable to open, close, or otherwise adjust a connection between inner tube lumen 150 and inner tube port 152.

For example, during a PCNL procedure, a user may apply energy to break up one or more kidney stones. The user may insert medical device 110 into a patient cavity through an insertion device, for example, an insertion sheath or a nephroscope. A suction source may be coupled to port 124, and an irrigation source may be coupled to inner tube port 152. The user may activate the suction, for example, by depressing trigger 128, in order to remove small stone fragments, tissue, or other occluding material. The user may also deliver irrigation fluid through inner tube port 152, inner tube lumen 150, and inner tube 134 in order to, for example, balance the pressure within the patient's cavity during the suction and help prevent the patient's cavity from collapsing under the suction pressure. Delivering irrigation fluid may also aid the user in visualizing the patient's cavity and any material within the cavity. The user may actuate handle 116 by compressing distal arm 118 and proximal handle 120 to extend drive wire 114 distally and to expand retrieval basket 132 to capture a larger stone or piece of material. Drive wire 114 may then be withdrawn proximally into inner tube 134 by allowing joint 122 to bias distal arm 118 and proximal arm 120 toward their respective equilibrium positions, enclosing the larger stone or piece of material within inner tube 134. The stone or piece of material may be removed from the patient by withdrawing medical device 110 from the insertion sheath or nephroscope.

In another aspect, the user may apply suction through port 124 and outer tube 112 to draw a larger stone or piece of material to abut or stick to the distal end of outer tube 112. While maintaining the suction, the user may remove medical device 110 from the insertion sheath or nephroscope, with the stone sticking to the distal end of outer tube 112. Furthermore, suction through either outer tube 112 or inner tube 134 may help draw a stone or material toward medical device 110 to then be captured and removed with retrieval basket 132.

Figure 4:
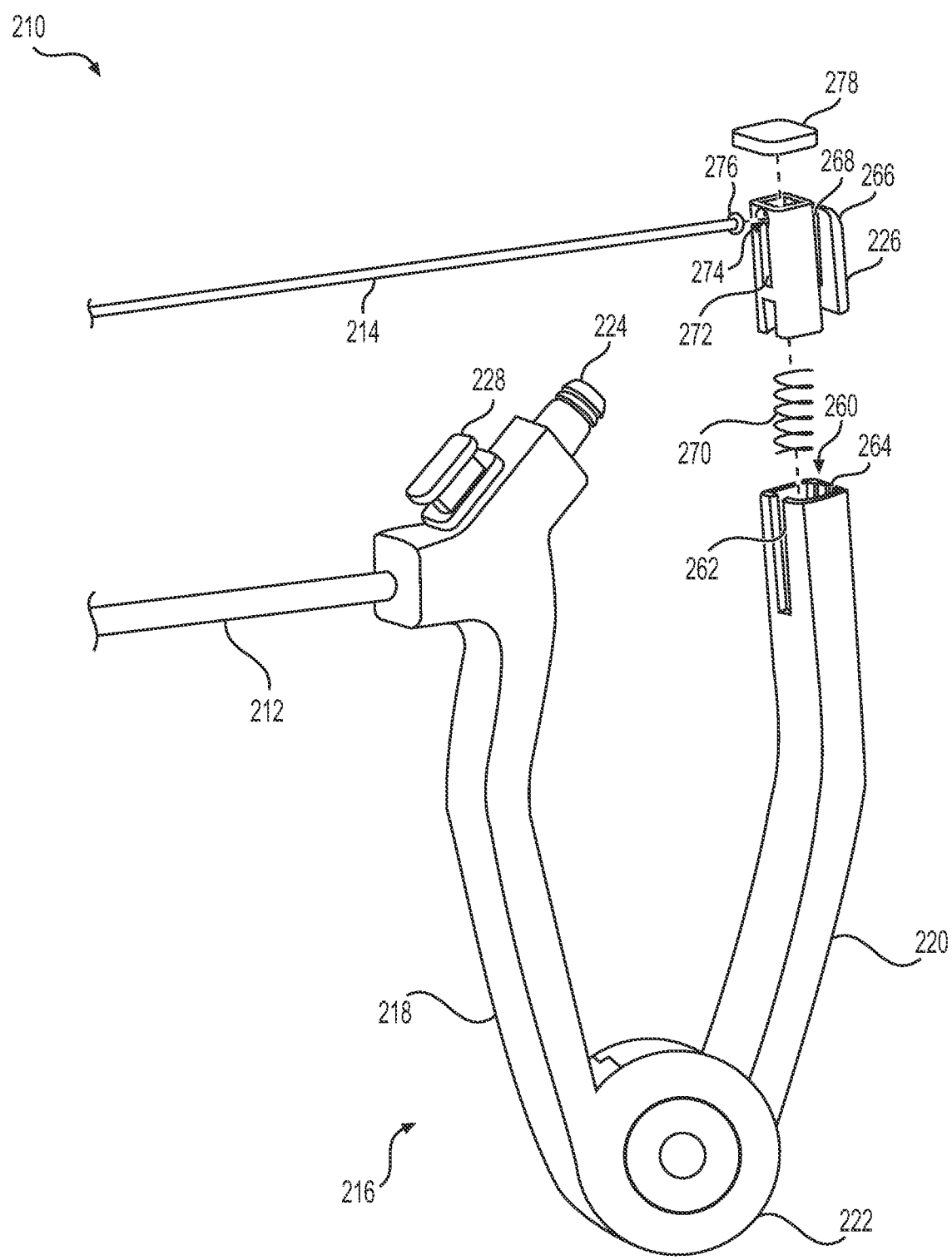
FIG. 4 illustrates a perspective and partially exploded view of a portion of an additional medical device, according to additional aspects of the present disclosure.

Turning now to FIG. 4, this figure illustrates additional aspects of this disclosure that may be incorporated in any of the aforementioned embodiments, with similar elements to medical device 10 shown by 200 added to the reference numbers. In particular, FIG. 4 shows a partially exploded view of a proximal portion of medical device 210 with drive wire 214 separate from outer tube 212 and handle 216. As in the previous embodiments, distal arm 218 of handle 216 includes port 224 and trigger 228.

Proximal arm 220 of handle 216 includes an open top end 260 that includes a first slot 262 and a second slot 264 opposite first slot 262. Drive wire clip 226 may be sized to fit within top end 260 between first slot 262 and second slot 264. Drive wire clip 226 may include a thumb pad 266 and a protrusion 268 extending proximally such that, when coupled to handle 216, drive wire clip 226 may slide within open top end 260 with protrusion 268 through second slot 264. The movement of drive wire clip 226 relative to proximal arm 220 may be biased by a spring 270.

Drive wire clip 226 also includes a wire slot 272 substantially aligned with and narrower than first slot 262. Wire slot 272 extends vertically through a distal portion of drive wire clip 226 and includes a release portion 274. Drive wire 214 includes a coupling portion 276 at a proximal portion of drive wire 214. Medical device 210 further includes a cap 278, which may be snap coupled or otherwise secured over open top end 260 of proximal arm 220 to enclose drive wire clip 226 and spring 270 within open top end 260.

As shown in FIG. 4, drive wire 214 may be coupled to drive wire clip 226 with coupling portion 276 fitting within wire slot 272. Drive wire 214 may be coupled to drive wire clip 226 by inserting coupling portion 276 through release portion 274. In an equilibrium position, spring 270 and cap 278 may position drive wire clip 226 within open top end 260 such that drive wire 214 is within wire slot 272 below release portion 274. Coupling portion 276 helps to ensure that drive wire 214 remains coupled to drive wire clip 226 within proximal arm 220. The user may act on handle 216 as discussed above to deliver suction or irrigation and to extend a distal end of drive wire 214 distally beyond outer tube 212 and inner tube (not shown). In an instance where it is necessary or desired to disconnect a proximal end of drive wire 214 from handle 216, the user may depress drive wire clip 226 by sliding thumb pad 266 and protrusion 268 downward within second slot 264, compressing spring 270. Drive wire 214 is at least partially rigid, so as drive wire clip 226 slides downward, drive wire 214 and coupling portion 276 remain stationary within drive wire clip 224. If drive wire clip 226 is fully depressed, coupling portion 276 may align with release portion 274. Then, forces acting on drive wire 214 from a distally positioned stone or imparted on the proximal end of drive wire 214 by the user may slide coupling portion 276 out of release portion 274, disconnecting the proximal end of drive wire 214 from drive wire clip 224 and proximal arm 220. Slidable drive wire clip 226 may help a user to disconnect drive wire 214 without the assistance of another medical professional and without the need to remove an additional element or piece from medical device 210.

While release portion 274 and coupling portion 276 are shown as circular in FIG. 4, this disclosure is not so limited. In one aspect, both elements may be triangular, rectangular, pentagonal, etc., or otherwise mirror each other such that drive wire 214 may be coupled within wire slot 272 and be released from drive wire clip 226 through release portion 274 when drive wire clip 226 is depressed.

Figure 5A:
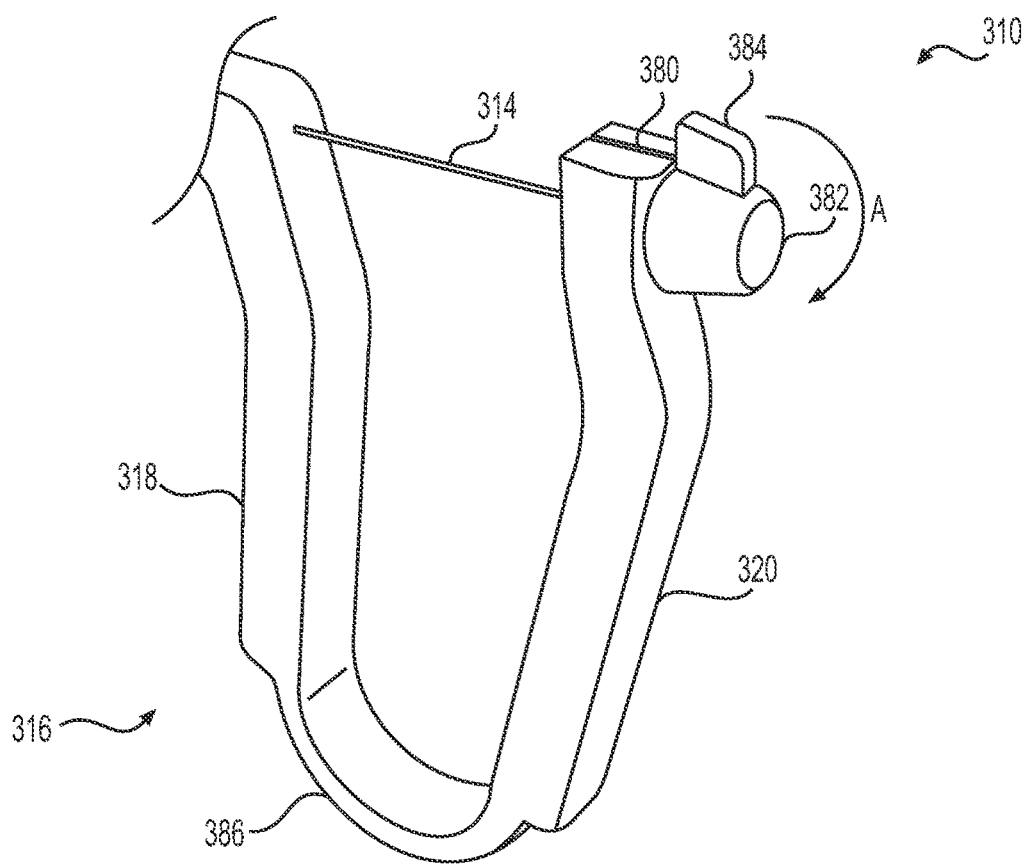
FIGS. 5A and 5B illustrate perspective views of a portion of a further medical device, according to further aspects of the present disclosure.
Figure 5B:
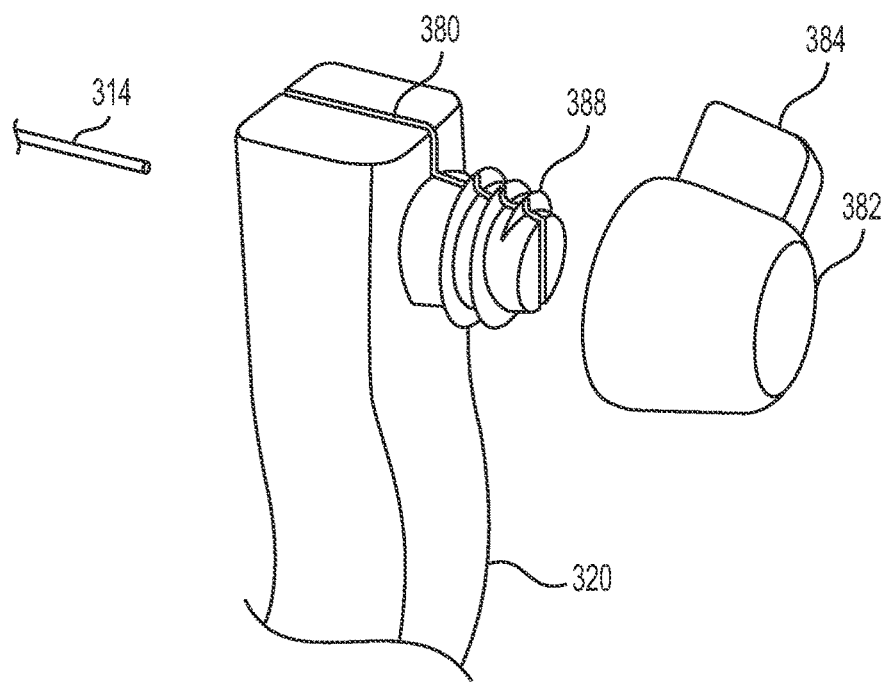

FIGS. 5A and 5B illustrate additional features according to aspects of this disclosure. Specifically, FIGS. 5A and 5B illustrate additional features that may aid a user in coupling and uncoupling a drive wire and a handle, with similar elements to medical device 10 shown by 300 added to the reference numbers. FIGS. 5A and 5B show perspective views of a portion of medical device 310 with drive wire 314 coupled to handle 316. In particular, proximal arm 320 includes a wire slit 380 in a top portion of proximal arm 320. A screw tab 382 may be coupled to proximal arm 320, and with screw tab 382 coupled to proximal arm 320, drive wire 314 may be pinched or otherwise secured within wire slit 380 (FIG. 5A). In particular, wire slit 380 may be biased outwardly to form a wider slit, and screw tab 382 may be attached to a threading 388 (FIG. 5B) to pinch or compress wire slit 380 to secure drive wire 314 to proximal arm 320. Screw tab 382 may include an internal threading (not shown) and a projection 384, which may help a user actuate, grip, or rotate screw tab 382. Screw tab 382 may be couplable to a threading 388 on proximal arm 320 (FIG. 5B). In one aspect, a user may hold handle 316 in one hand, and may use his or her other hand to rotate screw tab 382. In another aspect, the user may hold handle 316 in one hand, and may use the thumb of the same hand to rotate screw tab 382.

With drive wire 314 secured within wire slit, a user may deliver and actuate medical device 310 as discussed above in order to extend the distal end of drive wire 314. Although medical device 310 includes a bend joint 386 connecting distal arm 318 and proximal arm 320, bend joint 386 may bias handle 316 to a retracted position as discussed above with respect to joint 22.

If it is necessary or desired to disconnect drive wire 314 from handle 316, the user may rotate screw tab 382, for example, in direction A. Rotating screw tab 382 may disconnect screw tab 382 from a threading 388 on proximal arm 320. As shown in FIG. 5B, wire slit 380 may extend through a middle portion of threading 388. With screw tab 382 disconnected, wire slit 380 may expand or widen, allowing drive wire 314 to move within and disconnect from wire slit 380. Therefore, the user may disconnect drive wire 314 from proximal arm 320 without the assistance of another medical professional. Furthermore, if it is desired, the user may recouple drive wire 314 in slit 380 by positioning drive wire 314 in slit 380 and screwing screw tab 382 over threading 388 to pinch or compress slit 380 and couple drive wire 314 to proximal arm 320.

FIGS. 6A and 6B illustrate additional features according to aspects of the present disclosure. Specifically, FIGS. 6A and 6B illustrate additional features that may aid a user in capturing or releasing material, for example, a kidney stone, with similar elements to medical device 10 shown by 400 added to the reference numbers. FIGS. 6A and 6B show side and perspective views of a portion of medical device 410 with outer tube 412 and drive wire 414 coupled to handle 416.

In particular, handle 416 includes a lever 490 slidably positioned within a slot 492. Lever 490 and slot 492 may be positioned on a distal extension 494 extending from distal arm 418 of handle 416. Slot 492 may be located in a bottom portion of distal extension 494. In one aspect, lever 490 is fixedly coupled to outer tube 412, such that movement of lever 490 within slot 492 translates outer tube 412. For example, if retrieval basket 432 is extended, a user may move lever 490 proximally in direction B, causing outer tube 412 to retract proximally and, thus, causing retrieval basket 432 to further expand in size and/or change shape. In one aspect, retrieval basket 432 may include a shape memory alloy that expands or changes shape as retrieval basket 432 is uncovered. The proximal movement of lever 490 may be biased by an internal spring (not shown) within distal arm 418 or distal extension 494. It is noted that drive wire 414 passes through outer tube 412 and lever 492 to connected to proximal arm 420 as discussed above, for example, via drive wire clip 426.

Moreover, it is noted that the position and orientation of lever 490, for example, proximate to and parallel to distal arm 418, may help to allow a user to comfortably hold and manipulate the elements of medical device 410. In one aspect, the user may hold distal arm 418 and proximal arm 420 of medical device 410 in one hand, and the user can use one or more fingers of the same hand or the user's other hand to manipulate lever 490. It is noted that lever 490 and slot 492 may be positioned on distal extension 494 in different locations or positions, for example, on top or side portions of distal extension 494. Medical device 410 may also include a locking device (not shown) in order for a user to selective lock lever 490 in various positions within slot 492. Additionally, slot 492 may include one or more indications or indicia adjacent to a length of slot 492 to indicate to the user various positions that correspond to various sizes or shapes of retrieval basket 432.

As such, a user may deliver and actuate medical device 410 as discussed above in order to extend the distal end of drive wire 414 by relative movement of distal arm 418 and proximal arm 420. Extending the distal end of drive wire 414 extends retrieval basket 432, for example, a self-expanding basket, in order to capture material within retrieval basket 432. In some instances, the material may be too large or oddly shaped to be withdrawn through outer tube 412, an internal sheath, or another insertion device used during the procedure to deliver medical device 410. In such an instance, the user may seek to release the material from retrieval basket 432. As such, the user may proximally retract lever 490, retracting outer tube 412 and expanding retrieval basket 432, which may help to release the material from retrieval basket 432.

As shown in FIG. 6A, retrieval basket 432 may include a first size and shape, which corresponds to handle 416 being fully contracted. Retrieval basket 432 may transition to retrieval basket 432'. Retrieval basket 432' includes a second size and shape, and corresponds to handle 416 (i.e., distal arm 418 and proximal arm 420) being fully contracted and lever 490 being fully proximally retracted. For example, retrieval basket 432 may include a diameter C of approximately 16 mm, and retrieval basket 432' may include a diameter D of approximately 20 mm. In another aspect, retracting lever 490 and outer tube 412 proximally may both expand and change the shape of retrieval basket 432. For example, although not shown, a first shape may be substantially elliptical (e.g., a 16 mm elliptical basket), and second shape may be substantially spherical or rounded (e.g., a 20 mm spherical basket). A smaller size or elliptical shape may include smaller spaces or gaps between struts of retrieval basket 432, and a larger size or spherical shape may include larger spaces or gaps between struts of retrieval basket 432'. As such, one size or shape may be helpful in retaining a smaller stone or piece of material, while another size or shape may be helpful in releasing a larger stone or piece of material.

In another aspect, the user may utilize the lever to extend and expand retrieval basket 432 such that retrieval basket 432 is positioned distally beyond the material to be captured. The user may then capture the material by releasing lever 490 such that the material is captured as retrieval basket 432 reduces in size and retracts proximally, moving toward outer tube 412 or another insertion device.

FIGS. 7A and 7B illustrate additional features according to aspects of the present disclosure. Specifically, FIGS. 7A and 7B illustrate additional features that may aid a user in manipulating a retrieval basket while capturing or releasing material, for example, a kidney stone, with similar elements to medical device 10 shown by 500 added to the reference numbers. FIGS. 7A and 7B show side and cross-sectional views of a portion of medical device 510 with outer tube 512 and drive wire 514 coupled to handle 516.

FIG. 7A illustrates a portion of medical device 510 with handle (not shown) compressed to extend retrieval basket 532 distally from outer tube 512. Similar to medical device 410, medical device 510 includes a distal extension 594 extending from distal arm 518. Outer tube 512 is fixed to or otherwise positioned within distal extension 594. Medical device 510 further includes a rotary knob 596. Rotary knob 596 may be positioned within a U-shaped opening between a proximal portion 594A and a distal portion 594B of distal extension 594. Proximal portion 594A and distal portion 594B are connected by a connecting or bridge element 598 that encloses a portion of rotary knob 596 by extending between, for example, bottom portions of proximal portion 594A and distal portion 594B. Although not shown, medical device 510 may include an additional bridge element 598 connecting top portions of proximal portion 594A and distal portion 594B to surround rotary knob 596 on both a bottom side and a top side.

As shown in FIG. 7B, rotary knob 596 radially surrounds a portion of drive wire 514. Additionally, drive wire 514 may include a shaft 501 radially surrounding a portion of drive wire 514, between drive wire 514 and rotary knob 596. Shaft 501 may be secured to a portion of drive wire 514 via adhesive, welding, crimping, or otherwise fixedly coupled. Shaft 501 and rotary knob 596 may include at least one engaging surface such that rotation of rotary knob 596 rotates shaft 501, and thus also rotates drive wire 514 and retrieval basket 532. For example, an outer surface of shaft 501 and an inner surface of rotary knob 596 may be square or rectangular (FIG. 7B), may be pentagonal, hexagonal, etc. In another aspect, the outer surface of shaft 501 may include a protrusion, and the inner surface of rotary knob 596 may include an indentation to receive the protrusion, or vice versa. In any of the aforementioned aspects, the engagement between rotary knob 596 and shaft 501 allows for shaft 501 to slide longitudinally through, proximally or distally, rotary knob 596. Furthermore, as shown in FIG. 7B, shaft 501 extends longitudinally around drive wire 514 longer than the length of rotary knob 596. For example, with handle 516 of medical device 510 not compressed and with distal arm 518 and proximal arm (not shown) in an equilibrium position, shaft 501 may extend from a distal edge of rotary knob 596 to just distal to the coupling of drive wire 514 to the proximal arm. Alternatively, shaft 501 may also be coupled to the proximal arm. As drive wire 514 and shaft 501 pass through rotary knob 596 due to action on handle 516 of medical device 510, rotary knob 596 and shaft 501 maintain at least one engaging surface. Therefore, the user may rotate rotary knob 596 to rotate shaft 501 and drive wire 514, and thus rotate retrieval basket 532, throughout the extension and retraction of drive wire 514. Although not shown, medical device 510 may further include a locking mechanism to secure a position of rotary knob 596 relative to distal extension 594.

A user may deliver and actuate medical device 510 as discussed above in order to extend the distal end of drive wire 514 by relative movement of distal arm 518 and proximal arm (not shown). Extending the distal end of drive wire 514 extends retrieval basket 532, for example, a self-expanding basket, in order to capture material within retrieval basket 532. Additionally, extending the drive wire 514 slides shaft 501 distally through rotary knob 596. During any stage of the extension and expansion, the user may act on rotary knob 596 to rotate drive wire 514 and retrieval basket 532 due to the interlocking arrangement of shaft 501 and rotary knob 596. For example, rotating rotary knob 596 in direction E also rotates retrieval basket in direction E (FIG. 7A). The user may act on rotary knob 596 with a finger or fingers of one hand while holding handle 516 in the same hand. Alternatively, the user may act on rotary knob 596 with a finger or finger of the user's other hand to rotate retrieval basket 596. Rotation of retrieval basket 596 may help a user capture or release a kidney stone or other piece of material by allowing the user to selectively position the struts of retrieval basket 596 relative to the material without rotating his or her hand or wrist. Therefore, drive wire 514 and retrieval basket 532 include two degrees of movement—longitudinal translation via relative compression of distal arm 518 and the proximal arm, and rotation via action on rotary knob 596.

The disclosed medical devices 10, 110, 210, 310, 410, and 510 and portions thereof shown in the figures and discussed above may allow a user to control the suction, irrigation, and extension of medical devices to a patient's lumen. The devices 10, 110, 210, 310, 410, and 510 and portions thereof may also help enable efficient and effective procedures to remove material from a patient, while also providing irrigation to maintain a safe pressure within the cavity and help prevent the patient's lumen from collapsing. The irrigation may also enhance visualization during the medical procedure. For example, a user may insert a nephroscope to a patient's kidney and apply energy to break up one or more kidney stones. The user may remove the energy source and then insert one of medical devices 10, 110, 210, 310, 410, or 510 through the nephroscope. The user may remove smaller stone particles by delivering suction through port 24 and outer tube 12. Without repositioning medical device 10, 110, 210, 310, 410, or 510, the user may compress the handle to extend a retrieval basket 32 or other medical device to capture a larger piece of stone material, with the bias of the handle withdrawing the material within inner tube 34. The user may then remove the medical device from the nephroscope, with the stone material enclosed within inner tube 34.

In an additional aspect, the captured stone material may be too large to be enclosed within inner tube 34. In this aspect, medical devices 210 and 310 illustrate aspects that may be used to disconnect the drive wire 214, 314 and/or dismantle the medical devices. Such aspects may be used to disconnect the drive wire and manually push or pull the drive wire. Additionally, such aspects may be used to disconnect the drive wire and remove the remainder of the medical device from the nephroscope in order for a lithotripter or other energy source to be reinserted and deliver additional energy to the stone material captured within the retrieval basket. Moreover, these aspects may be performed by a user without the assistance of another medical professional and without the need to remove an additional element or piece from the medical device.

Medical devices 410 and 510 illustrate aspects that may be used to capture and release the stone material. For example, medical device 410 may aid in the capture or release of the stone material by allowing the user to manipulate the size and shape of retrieval basket 432 through action on lever 490 to retract outer tube 412. Furthermore, medical device 510 may also help a user in the capture or release of the stone material by allowing the user to manipulate the position of drive wire 514, and thus retrieval basket 534, by rotating rotary knob 596. Rotating retrieval basket 534 may help the user to position individual struts of retrieval basket 534 relative to the stone material. A user may be able to rotate retrieval basket 596 by rotating rotary knob 596, and thus not have to rotate his or her hand or wrist while holding medical device 510. It is also noted that, although not shown, medical devices 410 and 510 may include inner tubes, ports, and other features discussed with respect to medical devices 10, 110, 210, and 310 in order to deliver irrigation and suction through outer tube 412, 512 or to couple and uncouple drive wire 414, 514 to the proximal arm of handle 416, 516.

While much of this disclosure is directed to percutaneous nephrolithotomy (PCNL) with or without lithotripsy, it is further contemplated that the systems and procedures discussed herein may be equally applicable to other material removal procedures. For example, the devices and methods discussed above may be used during a ureteroscopic kidney stone removal. The devices and methods discussed above may also be used in procedures to remove ureteral stones, gallstones, bile duct stones, polyps, etc.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A medical device comprising:
   a handle including a proximal arm and a distal arm, wherein the proximal arm and the distal arm are pivotable via a joint, and wherein the distal arm includes a handle port;
   an outer tube coupled to the distal arm and fluidly coupled to the handle port;
   an inner tube positioned within the outer tube; and
   a drive wire, wherein a portion of the drive wire is positioned within the inner tube, and wherein a different portion of the drive wire extends proximally of the distal arm and is coupled to the proximal arm,
   wherein the drive wire is releasably coupled to the proximal arm of the handle via a depressible and slotted drive wire clip, and wherein the drive wire clip is biased toward an extended position by a spring within the proximal arm.

2. The medical device of claim 1, further including a mechanism to open or close a connection between the handle port and the outer tube.

3. The medical device of claim 2, wherein the mechanism is a trigger.

4. The medical device of claim 2, wherein the mechanism is a dial, and wherein the connection between the handle port and the outer tube includes a variable opening.

5. The medical device of claim 1, further including an inner tube port in the distal arm that is fluidly connected to the inner tube.

6. The medical device of claim 5, wherein the handle port is configured to be connected to a suction source to deliver suction through the outer tube, and wherein the inner tube port is configured to be connected to an irrigation source to deliver irrigation through the inner tube and around the drive wire.

7. The medical device of claim 6, further including a mechanism to open or close a connection between the inner tube port and the inner tube.

8. The medical device of claim 1, wherein the medical device is configured to be held in a user's hand, and wherein the drive wire clip is configured to be actuated by a thumb of the user's hand.

9. The medical device of claim 1, wherein the inner tube is secured within the outer tube through laser welding; and wherein the joint includes a torsion spring.

10. The medical device of claim 9, wherein a distal end of the drive wire includes an expandable retrieval basket; and wherein a proximal portion of the distal arm includes a seal; and
wherein the drive wire is movable through the seal.

11. A medical device handle comprising:
    a distal arm, including a first internal lumen fluidly connected to a first port, and a second internal lumen fluidly connected to a second port;
    a proximal arm;
    an outer tube coupled to the first internal lumen;
    an inner tube within the outer tube and coupled to the second internal lumen;
    a drive wire clip, wherein the drive wire clip includes a slot and is depressible within a portion of the proximal arm; and
    a drive wire including an expandable end effector at a distal end of the drive wire, wherein a portion of the drive wire is positioned within the inner tube and moveable through the second internal lumen,
    wherein a proximal portion of the drive wire extends proximally of the distal arm and is releasably coupled to a distal portion of the proximal arm, wherein the drive wire is releasably coupled to the distal portion of the proximal arm via the drive wire clip, and wherein the drive wire clip is biased toward an extended position by a spring within the proximal arm;
    wherein the proximal arm and the distal arm are pivotable via a joint, and wherein pivoting of the proximal arm and the distal arm extends or retracts the drive wire from a distal end of the inner tube; and
    wherein the drive wire clip is operable to disconnect the drive wire from the proximal arm.

12. The medical device handle of claim 11, further including a mechanism to adjustably control a flow of suction or irrigation through the first internal lumen.

13. The medical device handle of claim 11, further including a first tube coupled to the first internal lumen and a second tube coupled to the second internal lumen, wherein the second tube is positioned within the first tube; and
    wherein the first port is configured to be connected to a suction source to deliver suction through first internal lumen and the outer tube to surround the inner tube.

14. The medical device handle of claim 11, wherein the drive wire clip is movable within an opening in the proximal arm, wherein the slot of the drive wire clip includes a release portion, wherein the proximal portion of the drive wire includes a coupling portion configured to be retained within the slot and slide through the release portion, and wherein movement of the drive wire clip within the opening in the proximal arm positions the coupling portion within the release portion.

* * * * *